United States Patent [19]

Alvarez et al.

[11] 4,400,396

[45] Aug. 23, 1983

[54] ANTITHROMBOTIC TREATMENT WITH ORGANIC AMINE SULFITES AND BISULFITES

[75] Inventors: Jose A. A. Alvarez, Mexico City, Mexico; Ralph B. Thompson, Oak Brook, Ill.

[73] Assignee: T & R Chemicals, Inc., Clint, Tex.

[21] Appl. No.: 337,100

[22] Filed: Jan. 5, 1982

Related U.S. Application Data

[63] Continuation-in-part of Ser. No. 271,849, Jun. 16, 1981, abandoned, which is a continuation-in-part of Ser. No. 227,382, Jan. 2, 1981, abandoned, which is a continuation-in-part of Ser. No. 164,303, Jun. 30, 1980, abandoned.

[51] Int. Cl.$^3$ .................. A61K 31/13; A61K 31/095; A61K 31/185
[52] U.S. Cl. ................. 424/325; 424/248.5; 424/267; 424/315; 424/335
[58] Field of Search ............... 424/248.5, 267, 315, 424/325, 335

[56] References Cited

U.S. PATENT DOCUMENTS 2,367,302  1/1945  Moore .................. 424/331
3,836,639  9/1974  Teler .................... 424/101
3,906,109  9/1975  Roehm .................. 424/325

OTHER PUBLICATIONS

Chao., Thrombos, Haemostas (Stuttg) vol. 35, 1976, pp. 717-736.
Shulman, Chem. Abs., vol. 47, 1953, p. 9386.
Gunnison, Fd, Cosmet. Toxicol., vol. 19, 1981, pp. 667-682.
Elias, Abstract of Thromb. Diath. Haemorrh, vol. 18 (3-4), 1967, pp. 499-509.
Torda, Abs. of Anaesth. Intens. Care, 1, 293, (1973).
Bourbon, Abs. of J. Eur. Toxicol. vol. 4, No. 3, pp. 205-207 (1971).
Chem Abs., 9th Coll. Index, p. 37336CS & vol. 82, Ab. No. 107247f (1975).
Kikugawa, J. Pharm. Sci., vol. 61, 1972, pp. 1904-1907.
Rost, "Comparative Invst. of the Pharmacol. Effects of Organically Bonded Sulfurous Acids and of Neutral Sodium Sulfite", in Arb. A. D. Kaiserlichen Gesundheitsamte, vol. 21, 1904, p. 312.

Primary Examiner—Anna P. Fagelson
Attorney, Agent, or Firm—Cushman, Darby & Cushman

[57] ABSTRACT

Organic amine sulfites and bisulfites are found to demonstrate anticoaulgant and antithrombotic activity.

18 Claims, No Drawings

ANTITHROMBOTIC TREATMENT WITH ORGANIC AMINE SULFITES AND BISULFITES

CROSS-REFERENCE TO RELATED APPLICATION

This application is a continuation-in-part of my earlier filed U.S. patent application, Ser. No. 271,849, filed June 16, 1981, and now abandoned, this disclosure and contents of which are entirely incorporated herein by reference which in turn is a continuation-in-part of the earlier filed U.S. patent application Ser. No. 227,382, filed Jan. 2, 1981, and now abandoned, the disclosure and contents of which are entirely incorporated herein by reference which in turn is a continuation-in-part of my earlier filed U.S. patent application Ser. No. 164,303, filed June 30, 1980, abandoned, the disclosure and contents of which are entirely incorporated herein by reference.

BACKGROUND OF THE INVENTION

Inorganic salts of sulfurous acid have heretofore been discovered by one of us (Jose Antonio Arias Alvarez) to have anticoagulant and antithrombotic properties; see U.S. Ser. No. 164,845, filed June 30, 1980, now abandoned, refiled as U.S. Ser. No. 227,382, filed Jan. 22, 1981, now abandoned, refiled as U.S. Ser. No. 271,850 filed June 16, 1981, now abandoned, and refiled as U.S. Ser. No. 337,176 on Jan. 5, 1982.

So far as is now known, lower alkyl amine sulfite and bisulfite compounds have never previously been used as anticoagulant and/or antithrombotic agents.

Anticoagulants and antithrombotics are a group of compounds with diversified pharmacologic actions, used in a variety of chemical thrombotic disorders. Thrombotic disorders are generally divided into venous thrombosis and arterial occulsive disorders. Venous thrombosis of the lower extremities is important because it can cause pulmonary embolisms which may be fatal. Heparin and warfarin are commonly used in clinical medicine for prevention and treatment of deep venous thrombosis and pulmonary embolism. Their pharmacological actions are in the inhibition of blood coagulation activity (i.e., heparin) or of synthesis of coagulation factors (i.e., warfarin). Platelets play an important part in arterial thrombosis. Drugs that inhibit platelet aggregation are generally regarded as being potentially useful for prophylactic therapy of arterial thrombotic disorders, including, for example, stroke, myocardial infarction, and peripheral vascular disease. Despite the availability of many agents that possess anti-platelet aggregating properties, only few are currently under clinical trials (i.e., aspirin, dipyridamole, sulfinpyrazone). None of these exhibit unequivocal efficacy. Compounds with specific pharmacological action are urgently sought in order to provide better medical care for patients with these serious disorders.

An anticoagulant agent is a substance which inhibits coagulation of the blood.

An anti-platelet aggregating agent is a substance which inhibits platelet aggregation.

An antithrombotic agent is a substance which inhibits formation or development of a thrombus (or thrombosis). For present patent purposes, it will be understood that the term "thrombus" or equivalent includes the subject matter of the term "embolus" unless otherwise specifically indicated. In general, an antithrombotic agent may display in the presence of mammalian blood or appropriately prepared plasma anticoagulant activity and/or anti-platelet aggregating activity.

BRIEF SUMMARY OF THE INVENTION

There has now been discovered a class of organic agents, the members of which when introduced, as by ingestion, injection, absorption, or otherwise introduced into a mammal (including man), produce amelioration of a thrombotic condition in mammals (including man) when used in an antithrombotically effective amount as taught herein.

An active antithrombotic agent of the present invention is at least one lower alkyl amine sulfite compound represented by the formula:

(1)

where:
- $R_1$ is selected from the group consisting of lower alkyl radicals, cycloalkyl radicals containing from 6 to 10 carbon atoms each, lower monohydroxyalkyl radicals, and aralkyl radicals,
- $R_2$ is selected from the group consisting of lower alkyl radicals, lower monohydroxyalkyl radicals, and hydrogen,
- $R_1$ and $R_2$ together can constitute a ring selected from the group consisting of morpholine, piperidine, and hexamethyleneimine, provided that each such ring can be substituted on one of its carbon atoms by a lower alkyl radical,
- $R_3$ is selected from the group consisting of lower alkyl radicals lower monohydroxyalkyl radicals, hydrogen, and radicals of this formula:

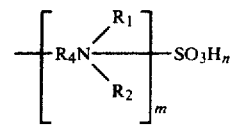

$R_4$ is a divalent saturated lower aliphatic radical,
m and n are integers, the sum of m and n is 2, and n is either 0 or 1.

The term "lower" as used herein unless the context specifically indicates otherwise has reference to a radical containing less than 11 carbon atoms.

Examples of suitable alkyl amine starting materials for making compounds of formula (1) include methyl amine, dimethyl amine, trimethyl amine, ethyl amine, tripentyl amine, monocyclohexyl amine, dimethylcyclohexyl amine, dimethyl ethyl amine, methylcyclohexyl amine, tri-n-butyl amine, and the like. Trimethyl amine salts tend, however, to be undesirable because of a strong associated odor, but with this exception, tri(lower alkyl)amines are one presently preferred class of starting materials for preparation of compounds of formula (1). Another presently preferred class of starting materials for such a preparation comprises monoalkyl amines having from 5 through 10 carbon atoms per molecule, such as mono-n-octyl amine, and the like. Examples of suitable diamine starting materials for making compounds of formula (2) include:

ethylene diamine
hexamethylene diamine
1,2-propylene diamine
tetramethyl ethylene diamine
N,N¹-dimethyl ethylene diamine
N,N¹-dibenzyl ethylene diamine
and the like.

Antithrombotic agents of this invention are used in both arterial thrombosis and venous thrombosis. Examples of clinical thrombotic conditions include stroke (such as a cerebral vascular thrombosis), myocardial infarction (coronary artery disease), peripheral vascular disease, cardiac valve replacement, deep vein thrombosis, pulmonary embolism, and the like.

The mechanisms by which the active agents function is presently unknown; however, an inhibition of platelet aggregation and prolongation of normal blood coagulation time appear to be associated with use thereof in the manner taught by the present invention.

In one aspect, the present invention is directed to the use of certain bisulfite and sulfite compounds as antithrombotic agents in human medicine.

In another aspect, the present invention is directed to a method for control, and/or prevention of, an embolus or a thrombus in man by oral ingestion and/or injection of a pharmaceutically effective amount of an amine bisulfite and/or other compound(s) within the scope of active agents of this invention.

In another aspect, the present invention provides symptomatic and objective improvement in a thrombotic (including cardiovascular) disease condition, such as, for example, an abnormal coagulation, or an intravascular thrombosis, in man. By the term "symptomatic improvement", as used herein, reference is had to an improvement in a patient's subjective symptoms (e.g., as reported by the patient). By the term "objective improvement", as used herein, reference is had to a measurable and objective change in a patient's condition.

Naturally, in active antithrombotic agent of this invention is used, if at all in a mammal, at a pharmaceutically effective dose rate, that is at a dose rate which is below the level of toxicity or of production of undesired side effects. Because of biological complexities, the complete biological effects of the active agents of this invention are not now known.

Other and further aspects, objects, purposes, advantages, aims, utilities, features and the like will be apparent to those skilled in the art from a reading of the present specification.

DETAILED DESCRIPTION

More particularly, this invention concerns a process for treating a human or other mammal for a thrombotic condition wherein there is introduced orally, by absorption, by injection or otherwise into such mammal a pharmaceutically effective amount of active agent as an antithrombotic.

Sulfite and/or bisulfite anions do not normally occur in human tissues or blood, so far as is now known.

In medicine, for example, arterial thrombosis is diagnosable by clinical manifestations, by arteriography, and recently, by an indium 111 platelet labeling technique (see, for example, the article entitled "Differential Effects of Two Doses of Aspirin on Platelet Vessel Wall Interaction In Vivo" by K. K. Wu et al being published in the Journal of Clinical Investigation, August, 1981.

Also, in medicine, for example, it is detectable from patient conditions symptomatically perceivable by a skilled medical practioner and well known to the art of medicine. Objectively, several methods including venography, impedance plethysmography, doppler ultrasound, and the $^{125}$I-fibrinogen test; see, for example, the article Kakkar, Archives of Surgery, Vol., 104, pg. 152 (1972) and Kelton, J. G. et al, Journal of Clinical Investigation, Vol. 62, pgs. 892–895 (1978).

By the term "thrombotic condition" as used herein, reference is had both to:

(a) an existing thrombus (including an embolus); and/or (b) an incipient thrombus (including an incipient embolus.

An "incipient thrombus" or "incipient thrombotic condition", as such a term is used herein, can exist in a patient who has a predisposed condition for development of a thrombotic condition. For examples, in a diabetes mellitus, hyperlipedemia, and the like are conditions which predispose a patient to arterial thrombosis.

Those skilled in the practice of medicine routinely determine the presence of a thrombotic condition (including an actual thrombus) in a patient. Such a condition is determined for the present invention preferably by state of the art techniques. Such determination techniques are known to the prior art and do not at such constitute a part of the present invention.

Preferably, to practice this invention in vivo, one introduces at least one active agent of this invention into blood of a patient, such as a human, the equivalent of from about 1 to 100 milligram per kilogram of mammal body weight (including human) per day, though larger and smaller dose rates may be employed, if desired, within the spirit and scope of this invention. The exact amount or dose in any given case is selected so as to be sufficient and appropriate for achieving a desired antithrombotic effect. Injection is accomplished with an active agent in solution.

In general, to initiate practice of the present invention, such an introduction may be commenced at a dosage rate with the range above indicated as soon as a thrombotic condition (or a thrombus) is found to exist in a patient.

Thus, and for example, in a preferred practice of this invention, as a first step, a determination is made that a patient suffers from a thrombotic condition. Then, one starts orally feeding, injecting or the like such patient with at least one active agent of the present invention at an effective dose rate in the range above indicated. Presently, a more preferred dose rate is believed to be from about 4 to 50 mg/kg per day. Preferably, at least two or three spaced doses per day are employable, each such dose being conveniently administered around meal time. Any convenient dose arrangement can be employed.

Not uncommonly, it is desirable or necessary to start treatment immediately upon the discovery of a patient's thrombotic condition to avoid damage, injury, or perhaps even death of the patient, as from an embolus. If oral administration is not convenient or rapid enough for a situation, the active agent can be directly introduced by injection into a patient, if desired, such as intraveneously, intraperitoneally, intramuscularly, subcutaneously, or the like. Absorption through a membrane, such as a dermal layer, may also be used, as when an active agent is dissolved in an appropriate solvent.

Suppositories can be used to achieve absorption. When an active agent is so directly introduced, it is preferably dissolved in an aqueous medium wherein the total amount of active agent introduced into such medium wherein it is preferably within the range from about 1 to 15 weight percent (based on the total solution weight). Distilled water is a presently preferred solvent for such a medium. If desired, conventional, standardized aqueous media may be used as vehicles for such introduction; for example, standard saline solutions can be used as vehicles.

A present preference is to withdraw samples of blood from a patient undergoing treatment and to measure platelet aggregation. One method is described in the paper by Born, G. Nature 194, pp. 927–929 (1962) may be used for this purpose if desired.

After administration has started, the dose rate is preferably adjusted to a value which is sufficient to disrupt platelet function and/or coagulation factors and thereby achieve a desired antithrombotic effect.

An active agent of this invention, for example, is characteristically capable of exhibiting platelet aggregation both in vitro and in vivo. Also such an active agent is characteristically capable of lengthening both PT (prothrombin time) and PTT (blood partial thromboplastin time) in vitro. Dose rate of active agent is presently believed to be directly proportional to resulting effects upon blood factors, such as inhibition of platelet aggregation or the like. Consequently, under this preferred procedure, use of an active agent at a suitable dose for an individual patient ameliorates that patient's thrombotic condition.

Selected blood parameters of a patient are preferably determined before dosing with active agent is started, as when time permits. Preferably, a dose rate adjustment is accomplishable after administration of an active agent has commenced and is continuing. The amount of adjustment (or incremental change in dosage) is determinable by comparing a patient's measured values during administration of active agent to desired values (such as the patient's own starting corresponding values, normal species e.g. human, values, or the like). Inhibition of platelet aggregation can be used for measurements. Then, the deviation, if any, from the patient's such measured values is compared to such desired values (the patients starting values, normal species values, or the like). Then, a change in dose rate may be undertaken to correct for any deviation so determined.

For instance, in humans normal values for platelet aggregation are dependent upon the particular agent used for stimulation. For example, when adenosine diphosphate (ADP) at 3 millimolar concentration is employed, platelet aggregation values fall typically in the range between 50% to 100% of light transmission. Other stimulation agents include collagen, epinephrine, arachidonic acid, and the like.

Also, for instance, in humans, normal PT values are believed to fall in the range from about 11 to 13 seconds while normal PTT values are believed to fall in the range from about 25 to 41 seconds. If PT values and/or PTT values could be measured in a given patent, as for purposes of achieving a desired antithrombotic effectiveness, it is currently estimated that a lengthening of PTT value of from about 1.5 to 2 times a PTT value in such normal range in a given starting patient is appropriate (suitable) for antithrombotic effectiveness, which is equal to a lengthened PTT value for a given patient of from about 45 to 60 seconds; such an estimate is consistent, for example, with the lengthened PTT values achieved in the human use of heparin, a prior art agent sometimes previously employed as an antithrombotic agent. Similarly, it is currently estimated that a lengthening of PT value of about two times a PT value in such normal range in a given starting patient is appropriate (suitable) for antithrombotic effectiveness, which is equal to a lengthened PT value for a given patient of from about 22 to 26 seconds; such as estimate is consistent, for example, with the lengthened PT values achieved in the human use of coumadin (warfarin), a prior art agent sometimes previously employed as an antithrombotic agent. The active agents of the present invention, contrary to such prior art agents, appear to affect in vitro both PT and PTT values in a given patient, surprisingly. The mechanism by which the present active agents work is apparently substantially different from, and not comparable to, the prior art agents. Study and evaluation of the active agents of this invention continues.

Contrary to such prior agents (like heparin and coumadin), the active agents of the present invention appear to affect both blood coagulation factors and platelet aggregation. Conveniently and preferably, measurements of blood factors are carried out periodically, such as every 3 to 7 days, on a patient undergoing treatment under the practice of this invention.

An active agent can be orally consumed in the form of a capsule, a tablet, or the like, or in the form of a solution (e.g. aqueous). Also, an active agent can be injected in the form of an aqueous solution.

A particularly presently preferred antithrombotic field of use is in post operative patient treatment, as when arteries or deep veins may be involved in, or threatened by, a thrombotic condition.

By way of explanation, as those familiar with mammalian anatomy appreciate, the venous system of the lower extremities consists of superficial deep veins. Because of the manner in which the deep veins interconnect and supply blood to the heart and lungs, a thrombus occurring in the deep veins, but not in the superficial veins, can become the source of a blood clot which is moved through the veins and becomes lodged in the lungs, resulting in a pulmonary embolus, which can have obvious catastrophic effects (including causing death). Examples of deep veins include the iliac, the fermoral and the topliteal. The prevention of pulmonary emboli following surgery affecting the deep veins in the lower extremities is a significant medical problem. One solution to this problem is to prevent thrombi from occurring and/or developing in deep veins. To achieve this solution, active agents of this invention appear to be well suited. Thus, in one such mode of this invention, one achieves symptomatic and objective improvements in a patient during postoperative care following surgery affecting deep veins by inhibiting intravascular thrombosis (including embolism).

In one preferred mode of using this invention, an aqueous solution of from about 1 to 10 percent by weight of an active agent of this invention, is prepared. Then, such solution is orally consumed by a human or injected at the total (or accumulated) dose rate ranging from about 1.0 to 50 mg per each kg of body weight per day, more preferably in the form of at least two spaced doses per day, and still more preferably in the form of at least three spaced doses per day, such a dose being preferably taken around meal time. Solid or encapsulated active agents may be orally consumed alternatively.

Because of the tendency for active agents of this invention to undergo oxidation when in aqueous solution, it is presently common and even preferred in practicing this invention to minimize contact of such active agents with oxygen before use.

Compounds (active agents) of this invention are conveniently prepared by preparing an aqueous solution preferably using a purified or distilled water of a corresponding lower alkyl amine compound wherein such compound is present at a specified or calculated concentration, such as 10 weight percent. Then, through this solution is bubbled $SO_2$ gas until the resulting solution increases in weight to an extent sufficient to produce a weight corresponding to the desired sulfite or bisulfite salt. For example, to prepare a product solution which is substantially a bisulfite salt, twice as much weight increase is needed compared to the corresponding sulfite salt. If the starting amine is not fully soluble (or fully in a dissolved form) at the start of the sulfur dioxide gas addition (but is partially only dispersed or suspended in the aqueous phase), it becomes completely dissolved as $SO_2$ addition continues. The product solutions made from the various starting corresponding amines appear to exist most conveniently in solution form. Although some may be obtained as solids, e.g., monoethyl amine sulfite. Product solutions may be diluted to 1 to 10 percent and are preferably stored in closed containers to reduce oxidation.

The water used in a solution, of active agent, is preferably purified (e.g., filtered, deionized, distilled, or the like). After preparation, such a solution is preferably stored in a closed container to reduce oxidation.

Such an aqueous solution can be directly used in accordance with the teachings of this invention, in which such a solution can be dispensed dropwise, or such a solution can be encapsulated, or the like, and used as measured dosage units, as desired. For example, an aqueous solution containing 5 weight percent of active agent can be injected into a patient or it can be directly consumed by a patient as drops (e.g., from about 5 to 9 drops per meal for each of the two or three meals eaten by such patient per day, depending upon an individual patient's body weight, or the like).

Symptomatic improvement in varicose veins and in hemorrhoids has been observed when using an active agent.

A lengthened blood coagulation time in a mammal may be observable when such is given an active agent at the above indicated dose rate.

EMBODIMENTS

The present invention is further illustrated by reference to the following examples. Those skilled in the art will appreciate that other and further embodiments are obvious and within the spirit and scope of this invention from the teachings of these present Examples taken with the accompanying specification.

Preparation of Active Agents

Solution A Preparation

A 10 weight percent aqueous solution of triethyl amine bisulfite is prepared by bubbling $SO_2$ through an appropriate weight percent solution or dispersion of triethyl amine in water to form the desired aqueous product solution.

Solution B Preparation

Using the procedure of Solution A, a 10 weight percent aqueous solution of a diethyl amine bisulfite is prepared from diethyl amine.

Solution C Preparation

Using the procedure of Solution A, a 10 weight percent aqueous solution of isobutyl amine bisulfite is prepared from isobutyl amine.

Solution D Preparation

Using the procedure of Solution A, a 5 weight percent aqueous solution of n-octyl amine bisulfite is prepared from n-octyl amine.

Solution E Preparation

Using the procedure of Solution A, a 5 weight percent solution of tributyl amine bisulfite from tributyl amine is prepared.

Solution F Preparation

Using the procedure of Solution A, 5 weight percent solution of ethylene diamine bisulfite is prepared from ethylene diamine.

Solution G Preparation

Using the procedure of Solution A, a 5 weight percent solution or morpholine bisulfite is prepared from morpholine.

Solution H Preparation

Using the procedure of Solution A, a 5 weight percent solution of cyclohexyl amine bisulfite is prepared from cyclohexyl amine.

Solution I Preparation

Following the procedure of Solution A a 10 weight percent solution of triethyl amine sulfite is prepared from triethyl amine. One half as much $SO_2$ is consumed as compared to Solution A preparation.

Solution J Preparation

Into a suspension of N,N$^1$-dibenzyl ethylene diamine in water, gaseous $SO_2$ is bubbled to yield a 5 weight % solution of N,N$^1$-dibenzyl ethylene diamine bisulfite which has the following formula:

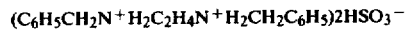

$(C_6H_5CH_2N^+H_2C_2H_4N^+H_2CH_2C_6H_5)2HSO_3^-$

EXAMPLE 1

The solution A is found to prolong PT and PTT in a dose related fashion. When added to human and to rabbit plasma in vitro, the agent triethyl amine bisulfite is found to significantly prolong PT and PTT values at a concentration of 0.5 mg/ml and the effects are directly proportional to dose. The agent is active in inhibiting various coagulation factors, including factors VII, IX, X, XI, and XII.

References for PT, PTT, and assays of all the coagulation factors can be found in a standard textbook, entitled "Human Blood Coagulation, Haemostasis and Thrombosis", edited by Rosemary Biggs, published by Blackwell Scientific Publications, Oxford, England (2nd Edition), pages 670–705, 1976.

EXAMPLES 2 AND 3

When Solution A and Solution I are each further similarly tested as in Example 1, prolongations of PT and PTT values at similar respective concentrations are observed, although somewhat different such values are obtained.

Data evaluated by the procedure above described is provided in Tables I and II below.

EXAMPLE 4

To demonstrate that triethyl amine sulfite and triethyl amine bisulfite have an effect upon blood coagulation factors, the data in Table I (below) for fibrinogen, Factor IX and Factor X using Biggs procedure are obtained. The results show a substantial effect on these factors with the bisulfite being more active.

EXAMPLE 5

To demonstrate reproducibility of the Biggs procedure, the work of Example 4 is repeated 5 times and the deviation is summarized and shown in Table II below.

EXAMPLE 6

A rabbit is injected with about 72 mg/kg of body weight of triethyl amine bisulfite. After a period of 5 hours, a blood sample was withdrawn and centrifuged at 1000 r.p.m. (220 g) for 10 minutes to give a platelet rich plasma.

EXAMPLE 7

Platelet rich plasma from rabbits and men was prepared by the centrifugation technique referenced in Example 6. Using ADP (adenosine diphosphate) as a stimulus rapid aggregation of platelets occurred. When the so stimulated blood had been treated with each of the agents of Example 6, there was a strong inhibition of platelet aggregation. This procedure is described in the article by Born in Nature, Vol. 194, pgs. 927–929 (1962). The results demonstrate that these agents cause inhibition of platelet aggregation in vitro.

Other stimuli, collagen and arachidonic acid, yielded similar results.

EXAMPLE 8

The procedure of Biggs is repeated for PT and PTT determination using various compounds of formula (1) with multiple replications for accuracy and consistency reasons. Compounds are generally effective in increasing PT and PTT. In general, the bisulfites of Formula (1) are somewhat more effective in increasing PT and PTT values than are the sulfites; the bisulfites of diamines (as compared to monoamines) are effective. Such an increase, indicates an anticoagulation effectiveness in vitro. The diallyl amine bisulfite is unexpectedly of low activity in increasing PT and PTT values.

The results are shown in Table III below.

Even though aromatic amines, such as aniline, form

TABLE I

EFFECT OF AMINE DERIVATIVES ON SELECTED COAG. FACTOR
FACTOR: FIBRINOGEN, FACTORS IX AND X

| EXP. NO. | AGENT RESIGNATION | FIBRINOGEN (%)[1] | FACTOR IX (%)[2] | FACTOR X (%)[3] |
|---|---|---|---|---|
| 4.1 | CONTROL | 205 | 50 | 100 |
| 4.2 | TRIETHYL AMINE BISULFITE | 125 | 14 | 14 |
| 4.3 | TRIETHYL AMINE SULFITE | 170 | 19 | 23 |

TABLE I FOOTNOTES:
[1] Values shown represent mean of two experiments
[2] Value of a single experiment
[3] Mean of three experiments

TABLE II

EFFECT OF AMINE DERIVATIVES ON COAGULATIONS

| | EXPERIMENT NO. | | | | | | | | | | | |
|---|---|---|---|---|---|---|---|---|---|---|---|---|
| | NO. 1 | | NO. 2 | | NO. 3 | | NO. 4 | | NO. 5 | | | |
| EXAMPLE NO. | PT (Sec) | PTT (Sec) | PT (Sec) | PTT (Sec) | PT (Sec) | PTT (Sec) | PT (Sec) | PTT (Sec) | PT (Sec) | PTT (Sec) | MEAN | LSD |
| 5.1 CONTROL | 12.9 | 36.7 | 12.9 | 36.2 | 11.4 | 36.4 | 12.0 | 36.0 | 12.1 | 38.9 | 12.3 ±0.6 | 36.8 ±1.2 |
| 5.2 TRIETHYLAMINE BISULFITE | 23.3 | 24.7 | 25.3 | 86.3 | 18.5 | 64.2 | 18.9 | 71.2 | 20.4 | 68.9 | 21.3 ±3.0 | 73.1 ±8.3 |
| 5.3 TRIETHYLAMINE SULFITE | 17.0 | 59.2 | 18.5 | 65.1 | 15.4 | 54.9 | 16.6 | 59.0 | 16.8 | 64.0 | 16.9 ±1.1 | 60.6 ±4.1 |

(1) PT = PROTHROMBIN TIME (WHICH MEASURES INTEGRITY OF THE EXTENSIC COAG. PATHWAY)
PTT = PARTIAL PROTHROMBIN TIME (WHICH MEASURES INTEGRITY OF THE INTRINSIC PATHWAY)

The material was evaluated for platelet aggregation by the method described in Born et al (ref. cited above) and it was found that aggregation of platelets was markedly decreased in comparison with an untreated rabbit. It is concluded that triethyl amine bisulfite is an agent which inhibits thrombotic condition formation in vivo.

Other amine bisulfites such as n-octyl amine bisulfite, and tri-n-butyl amine bisulfite also demonstrate similar inhibition of platelet aggregation when similarly tested.

active agents, the aromatic amines are believed to be excessively toxic for mammalian use in this invention; hence, such are not included within the scope of formula (1).

The alkanol amine bisulfites are of approximately the same activity as are the lower alkyl amine bisulfites.

EXAMPLE 9

To evaluate whether or not an amine moiety has an effect on blood factors some amines were evaluated as their hydrochlorides (as opposed to corresponding sulfites and bisulfites).

After their respective preparations the amine salts were evaluated by the Biggs method for their effect on PT and PTT. The data (results) shown in Table IV below shows that these hydrochlorides have no effect upon PT and PTT in vitro.

EXAMPLE 10

A rabbit (body weight about 2.4 kg) is continuously infused with aqueous triethyl amine bisulfite solution at a rate of 400 mg/kg/hr (0.92 gram per hour) for a time of three hours. The rabbit is then injected with fibrinogen labeled with $I^{125}$. After 5 hours, the animal is sacrificed and the radioactive fibrinogen accumulated on a damaged jugular vein is determined. The radioactivity on a contra-lateral (undamaged) jugular vein is also determined as a control. Concurrently, another rabbit has experienced the same procedure but receives only sodium chloride solution as a control. The rabbit from the normal saline solution had seven times as much radioactivity as his counterpart infused with triethyl amine bisulfite. It is concluded that triethyl amine bisulfite shows a definite positive antithrombotic effect in the jugular vein.

TABLE III

EFFECT OF AMINE BISULFITES ON BLOOD COAGULATION

| | PTT REPLICATIONS | | | PT REPLICATIONS | | |
|---|---|---|---|---|---|---|
| | 1 | 2 | 3 | 1 | 2 | 3 |
| 7.1 N—METHYL CYCLOHEXYL AMINE | 60.6 | 61.8 | 61.6 | 20.5 | 20.3 | 20.4 |
| 7.2 ALLYL AMINE | 47.1 | 46.9 | 44.9 | 16.1 | 16.0 | 15.6 |
| 7.3 TERT-BUTYL AMINE | 68.2 | 68.9 | 69.0 | 21.7 | 21.8 | 21.8 |
| 4.4 DIALLYL AMINE | 38.8 | 39.6 | 39.1 | 13.4 | 13.7 | 13.8 |
| 7.5 PYRIDINE | 80.0 | 71.1 | 59.8 | 29.3 | 27.8 | 27.2 |
| 7.6 N,N—DIMETHYL CYCLOHEXYL AMINE | 60.1 | 62.1 | 58.9 | 18.9 | 20.4 | 19.8 |
| 7.7 MORPHOLINE | 66.8 | 61.8 | 51.7 | 19.3 | 21.0 | 17.5 |
| 7.8 ANILINE | 45.4 | 44.9 | 42.9 | 16.0 | 16.9 | 16.0 |
| 7.9 ETHANOL AMINE | 65.3 | 66.1 | 61.1 | 19.3 | 20.5 | 18.4 |
| 7.10 CONTROL PLASMA | 37.5 | 39.5 | 37.8 | 12.8 | 12.8 | 13.1 |
| 7.11 4-METHYL MORPHOLINE | 63.5 | 61.3 | 60.6 | 21.3 | 21.5 | 20.4 |
| 7.12 DIETHANOL AMINE | 62.6 | 58.0 | 60.6 | 20.6 | 19.8 | 19.7 |
| 7.13 TRIETHANOL AMINE | 74.2 | 68.8 | 73.6 | 22.9 | 23.1 | 23.3 |
| 7.14 CONTROL PLASMA | 38.2 | 38.3 | 39.2 | 13.1 | 13.1 | 13.0 |

TABLE IV

EFFECT OF AMINE HYDROCHLORIDES ON BLOOD COAGULATION

| | PT | | | PTT | | |
|---|---|---|---|---|---|---|
| | 1 | 2 | 3 | 1 | 2 | 3 |
| 9.1 TRIETHYLAMINE HYDROCHLORIDE | 12.8 | 12.7 | 13.5 | 32.0 | 31.5 | 34.5 |
| 9.2 CYCLOHEXYL AMINE HYDROCHLORIDE | 13.8 | 13.6 | 13.5 | 32.5 | 32.7 | 34.3 |
| 9.3 ALLYL AMINE HYDROCHLORIDE | 13.2 | 13.2 | 14.4 | 31.6 | 30.5 | 32.4 |
| 9.4 DIALLYL AMINE HYDROCHLORIDE | 12.8 | 13.1 | 13.5 | 30.5 | 30.7 | 30.4 |
| 9.5 PYRIDINE HYDROCHLORIDE (CRYSTALS) | 12.9 | 12.8 | 14.0 | 31.3 | 31.1 | 32.2 |
| 9.6 PYRIDINE HYDROCHLORIDE (POWDER) | 12.6 | 12.6 | 13.8 | 30.5 | 30.8 | 31.1 |
| 9.7 CONTROL PLASMA | 13.0 | 12.5 | 13.5 | 31.5 | 31.3 | 31.2 |

When n-octyl amine bisulfite, tributyl amine bisulfite, diethanol amine bisulfite, and triethyl amine sulfite are similarly evaluated, it is concluded that such compounds also show a definite positive antithrombotic effect in the jugular vein.

EXAMPLE 11

In addition the solutions B and C both cause an increase in PT and PTT when added to plasma at 0.5 mg/ml.

EXAMPLE 12

Triethyl amine bisulfite is evaluated under in vitro conditions as an anti-indium[111] platelet labeling technique in rabbits (see Wu et al above cited). The material was administered by intravenous injection (127.39 mg/kg of body weight) equivalent to 0.01 molar concentrations in blood).

The active agent effected reduction of about 30% in accumulation of platelet thrombus. Another rabbit so tested, died.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not be be construed or interpreted as being restrictive or otherwise limiting of the present invention, except as it is set forth in the hereto-appended claims.

We claim:

1. A method for treating a thrombotic condition in a mammal comprising administering to said mammal an antithrombotically effective amount of at least one agent having the formula:

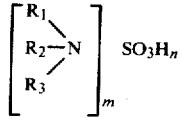

where;
  $R_1$ is selected from the group consisting of lower alkyl radicals, cycloalkyl radicals containing from 6 to 10 carbon atoms each, lower monohydroxyalkyl radicals, and aralkyl radicals,
  $R_2$ is selected from the groups consisting of lower alkyl radicals, lower monohydroxyalkyl radicals, and hydrogen,
  $R_1$ and $R_2$ together can constitute a ring selected from this group consisting of morpholine, piperidine, and hexamethyleneimine, provided that each such ring can be substituted on one of its carbon atoms by a lower alkyl radical, R$_3$ is selected from this group consisting of lower alkyl radicals lower monohydroxyalkyl radicals, hydrogen, and radicals of this formula:

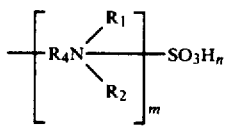

R$_4$ is a divalent saturated lower aliphatic radical, m and n are integers, the sum of m and n is 2, and n is either 0 or 1.

2. A method for treating a thrombotic condition comprising the step of orally feeding to a patient having a thrombotic condition from about 1 to 100 mg per kg of body weight per day in at least two spaced doses at least one agent having the formula:

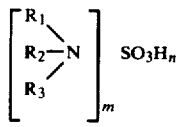

where:

R$_1$ is selected from the group consisting of lower alkyl radicals, cycloalkyl radicals containing from 6 to 10 carbon atoms each lower monohydroxyalkyl radicals, and aralkyl radicals, R$_2$ is selected from the group consisting of lower alkyl radicals lower monohydroxyalkyl radicals, and hydrogen, R$_1$ and R$_2$ together can constitute a ring selected from the group consisting of morpholine, piperidine, and hexamethyleneimine, provided that each such ring can be substituted on one of its carbon atoms by a lower alkyl radical, R$_3$ is selected from the group consisting of lower alkyl radicals lower monohydroxyalkyl radicals, hydrogen, and radicals of this formula:

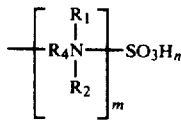

R$_4$ is a divalent saturated lower aliphatic radical, m and n are integers, the sum of m and n is 2, and n is either 0 or 1.

3. The method of claim 2, wherein after said feeding has started, said dose rate is adjusted to a value which is sufficient to cause a desired degree of change in at least one coagulation factor of such patient's blood.

4. The method of claim 3 wherein said adjusting is periodically performed.

5. The method of claim 1 wherein said agent is triethyl amine bisulfite.

6. The method of claim 1 wherein said agent is n-octyl amine bisulfite.

7. The method of claim 2 wherein said agent is in the form of an aqueous solution.

8. The method of claim 2 wherein said agent is orally fed to a patient at a dose rate of from about 20 to 50 mg per kg of body weight per day in at least two spaced doses.

9. The method of claim 1 wherein said thrombotic condition is demonstrated by the presence of an existing thrombus in such mammal.

10. The method of claim 1 wherein said thrombotic condition is demonstrated by the existence of an incipient thrombotic condition in such patient.

11. The method of claim 2 wherein the dose rate is adjusted to a value which is sufficient to disrupt platelet function, coagulation factors, or both, to achieve the desired antithrombotic effect.

12. A method for treating a thrombotic condition comprising the steps of injecting into a patient having a thrombotic condition at a dose rate of from about 1 to 100 mg per kg of body weight per day in at least two spaced doses at least one agent having the formula:

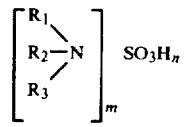

where:

R$_1$ is selected from the group consisting of lower alkyl radicals, cycloalkyl radicals containing from 6 to 10 carbon atoms each, lower monohydroxyalkyl radicals, and aralkyl radicals, R$_2$ is selected from the group consisting of lower alkyl radicals, lower monohydroxyalkyl radicals, and hydrogen, R$_1$ and R$_2$ together can constitute a ring selected from the group consisting of morpholine, piperidine, and hexamethyleneimine, provided that each such ring can be substituted on one of its carbon atoms by a lower alkyl radical, R$_3$ is selected from the group consisting of lower alkyl radicals lower monohydroxyalkyl radicals, hydrogen, and radicals of this formula:

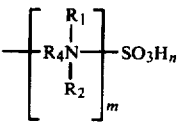

R$_4$ is a divalent saturated lower aliphatic radical m and n are integers, the sum of m and n is 2, and n is either 0 or 1.

13. The method of claim 12 wherein after said injecting has started said dose rate is adjusted to a value which is sufficient to cause a desired degree of change in at least one coagulation factor of such patient's blood.

14. The method of claim 13 wherein said adjusting is periodically performed.

15. The method of claim 12 wherein said adjusting is periodically performed.

16. The method of claim 12 wherein said agent is orally fed in a dose form selected from the group consisting of capsules and tablets.

17. A method for preventing thrombosis of deep veins following surgery in human patient comprising the step of treating said human patient post-operatively as a prophylaxis with an antithrombotically effective amount of at least one agent having the formula:

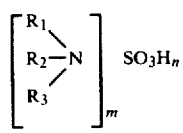

where:
- $R_1$ is selected from the group consisting of lower alkyl radicals, cycloalkyl radicals containing from 6 to 10 carbon atoms each, monohydroxyalkyl radicals, and aralkyl radicals,
- $R_2$ is selected from the group consisting of lower alkyl radicals, lower monohydroxyalkyl radicals, and hydrogen,
- $R_1$ and $R_2$ together can constitute a ring selected from the group consisting of morpholine, piperidine, and hexamethyleneimine, provided that each such ring can be substituted on one of its carbon atoms by a lower alkyl radical,
- $R_3$ is selected from this group consisting of lower alkyl radicals lower monohydroxyalkyl radicals, hydrogen, and radicals of this formula:

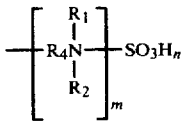

- $R_4$ is a divalent saturated lower aliphatic radical,
- m and n are integers, the sum of m and n is 2, and n is either 0 or 1.

18. A method of prolonging both the prothrombin time (PT) and partial thromboplastin time (PTT) of the blood or blood plasma of a mammal in need of such therapy, said method comprising administering to said mammal an antithrombotically effective amount of the agent of claim 1 and continuing said administration until the prothrombin time (PT) and thromboplastin time (PTT) are both prolonged as compared with PT and PTT values of the mammal's blood or blood plasma measured prior to initiating said therapy.

* * * * *